(12) United States Patent
Pini et al.

(10) Patent No.: US 9,821,140 B2
(45) Date of Patent: Nov. 21, 2017

(54) VARIABLE DIAMETER TUBE FOR USE IN A VASAL INSERTER FOR PERFORMING HEMODYNAMICS RESEARCHES AND RELATED OPERATIONS AND METHOD FOR MAKING SAID TUBE

(75) Inventors: Patrizia Pini, Novedrate (IT); Paolo Cremascoli, Novedrate (IT); Pedro Silva Orrego, Novedrate (IT)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 12/313,731

(22) Filed: Nov. 24, 2008

(65) Prior Publication Data

US 2009/0076455 A1    Mar. 19, 2009

(30) Foreign Application Priority Data

Dec. 10, 2007   (IT) .............................. MI2007A2309

(51) Int. Cl.
| | |
|---|---|
| *A61M 25/00* | (2006.01) |
| *A61M 25/06* | (2006.01) |
| *A61M 29/00* | (2006.01) |
| *A61B 17/34* | (2006.01) |

(52) U.S. Cl.
CPC .... *A61M 25/0043* (2013.01); *A61M 25/0023* (2013.01); *A61M 25/0662* (2013.01); *A61M 29/00* (2013.01); *A61B 17/3415* (2013.01); *A61B 17/3439* (2013.01); *A61B 17/3468* (2013.01); *A61B 2017/3433* (2013.01); *A61M 2025/0024* (2013.01); *A61M 2025/0687* (2013.01)

(58) Field of Classification Search
CPC ......... A61B 17/22031; A61B 17/3439; A61M 25/0043; A61M 2025/0681; A61M 25/0023; A61M 2025/0024; A61M 2025/0025; A61M 25/0029; A61M 2025/0034; A61M 2025/0035; A61M 25/0054; A61M 2025/0059; A61M 2025/006; A61M 2025/0177; A61M 2025/018; A61M 2025/0188; A61M 2017/3435; A61M 17/3439; A61M 2017/3441

USPC ...... 604/167.03, 164.03, 528–530, 533–539, 604/284, 104, 107, 6.16, 21, 532; 138/128, 137, 140–141

See application file for complete search history.

(56) References Cited

U.S. PATENT DOCUMENTS

| | | | | |
|---|---|---|---|---|
| 4,656,070 A | * | 4/1987 | Nyberg et al. | ................ 138/141 |
| 4,841,977 A | * | 6/1989 | Griffith et al. | ................ 600/439 |
| 5,318,588 A | * | 6/1994 | Horzewski et al. | .......... 606/198 |

(Continued)

OTHER PUBLICATIONS

Victrex, "Product Portfolio Summary." http://www.victrex.com/docs/literature-docs/Product%20Summary%20Card.pdf Retrieved Feb. 11, 2012.*

(Continued)

*Primary Examiner* — Nathan R Price
*Assistant Examiner* — Melissa A Snyder
(74) *Attorney, Agent, or Firm* — Stoel Rives LLP (57) ABSTRACT

A variable diameter tube for use in a vessel inserter for performing hemodynamics researches and related operations comprises two coupled different-characteristic materials which are coupled to one another to provide a single stretchable tube assembly.

10 Claims, 5 Drawing Sheets

(56) References Cited

U.S. PATENT DOCUMENTS

| | | | | |
|---|---|---|---|---|
| 5,406,871 A * | 4/1995 | Lambert, Jr. | | 138/103 |
| 5,676,659 A * | 10/1997 | McGurk | | 604/527 |
| 5,971,975 A * | 10/1999 | Mills et al. | | 604/527 |
| 6,312,443 B1 * | 11/2001 | Stone | | 606/198 |
| 6,585,719 B2 * | 7/2003 | Wang | | 604/525 |
| 6,984,201 B2 * | 1/2006 | Khaghani et al. | | 600/17 |
| 7,892,203 B2 * | 2/2011 | Lenker | A61B 17/3439 | 604/103.05 |
| 8,690,936 B2 * | 4/2014 | Nguyen | A61F 2/2427 | 606/191 |
| 2004/0087968 A1 * | 5/2004 | Core | | 606/108 |
| 2004/0131808 A1 * | 7/2004 | Schoenle et al. | | 428/35.7 |
| 2005/0080430 A1 * | 4/2005 | Wright et al. | | 606/108 |
| 2005/0149105 A1 * | 7/2005 | Leeflang | A61B 17/3439 | 606/198 |
| 2007/0119511 A1 * | 5/2007 | Donohue et al. | | 138/114 |

OTHER PUBLICATIONS

PEEK (PolyEtherEtherKetone) Specifications http://web.archive.org/web/20050306025200/http://www.boedeker.com/peek_p.htm (Mar. 6, 2005).*

* cited by examiner

VARIABLE DIAMETER TUBE FOR USE IN A VASAL INSERTER FOR PERFORMING HEMODYNAMICS RESEARCHES AND RELATED OPERATIONS AND METHOD FOR MAKING SAID TUBE

BACKGROUND OF THE INVENTION

The present invention relates to a variable or stretchable diameter tube for use in a vessel inserted for performing hemodynamic research and related operations. The invention also relates to a method for making said tube.

As is known, in a lot of surgical operations, an access to the hematic flow of the patient is achieved by puncturing an arterial vessel, typically a femoral or radial artery, while holding the vessel in a pervious condition by using a specifically designed introducing or inserter element or device.

Such an inserter element conventionally comprises a medical device adapted to be used in surgical operations, for example in a hemodynamics monitoring operation, an electrocatheter installing operation, a diagnostic test and any interventional surgical procedure in general.

In particular, said inserter is used for inserting, exchanging and monitoring other medical devices, for example catheters and electrodes, installed in a patient vessel.

Such an inserter has generally a variable length, within a length range from 15 to 40 cm.

The inserter, in particular, is characterized by its inner diameter (ID), which precisely defines the size of the device which can be introduced into a given vessel.

The inserter or introducer device is held in an installed condition through the overall surgical procedure duration, and it can be left in situ even for several days from the surgical intervention.

A prior inserter conventionally comprises an extruded tube element, which is extruded from a rigid and low friction material, such as FEP and PTFE, with a comparatively small thickness and a tapering distal part.

Some prior inserters have a stiffened or reinforced construction, that is comprise through their thickness a metal stiffening framework, to prevent the tube from undesirably bulging.

The proximal part of the inserter is usually coupled to a hemostatic valve, which comprises a plastics rigid component including an inner silicone diaphragm, designed for holding the inside of the inserter insulated from the outer environment.

Such a hemostatic valve operates to prevent blood from exiting the vessel and air from entering the latter.

Said valve consists of a pre-etched silicone septum assembly, allowing a preset device to be introduced thereinto, to be held coaxially therewith.

The second or other device, accordingly, is encompassed by a silicone material providing a tight sealing.

Generally, at a lateral position and downstream of said valve, is provided a line contacting the blood and to be used for continuously monitoring the patient blood pressure.

The above mentioned inserter or introducer device is usually located by using the so-called Seldinger's procedure.

According this installing method, the patient is punctured by a puncturing needle to penetrate a patient vessel.

Then, a guide wire having a suitable length is introduced into the needle, thereby locating said guide wire at a desired region of the vessel.

Then, the needle is withdrawn and the introducer-dilator system is caused to slide on the guide wire.

The dilator or dilatator device usually comprises a flexible hose, made of a low friction material, such as PTFE, with a tapering point designed for easily penetrating the vessel, and having a maximum outer diameter equal to the inner diameter of the introducer.

A specifically designed proximal system allows the dilator to be coupled or engaged to and disengaged from the introducer, upon withdrawing it from said introducer.

At the end of such an operation, only the introducer will be held within the patient vessel.

Accordingly, the introducer or inserter must have such a stiffness as to properly oppose the resilient strength of the vessel.

In this connection it should be pointed out that the above mentioned Seldinger's method allows the vessel to be opened by a dilating hole, and not by a cut-through arrangement.

Accordingly, such an operation exploits the deforming resilient capability of the vessel, which would be also very useful at the end of the procedure, for reclosing the vessel.

In this connection it should be apparent that an incision or cut-through would be much more difficult to be healed than a hole.

The vessel, in particular, is closed by applying a manual pressure force, or by a specifically designed closing system such as a percutaneous suturing system or collagen based system.

Sometimes, a set inserter or introducer device must be changed, by replacing it with a larger or smaller diameter inserter, for example for locating or installing ventricular aiding systems, to allow a larger diameter device to be driven through the vessel.

Up to now, such an operation involved a removal of the used inserter and a repetition of Seldinger's procedure, to just relocating the inserter.

At present, the tubes making the above mentioned medical devices have a cross-sectional fixed diameter, and are made by extruding, molding, blowing and dipping making methods.

More specifically, as an exemplary brief discussion, the above rigid tubes are made by extruding methods, the softer tubes, having elastic properties, being made by dipping methods, and the strong variable section tubes being made by extruding and blowing methods.

No polymeric material is at present known having shape memory capabilities while providing a satisfactory constructional stiffness: these properties, on the contrary, are well known in steel or nickel-titanium alloy mesh arrangements, which are of broad use in this field.

SUMMARY OF THE INVENTION

Accordingly, the aim of the present invention is to provide such a variable diameter rigid tubes which can be easily used as an inserter or introducing device in the medical field.

Within the scope of the above mentioned aim, a main object of the invention is to provide such a variable diameter rigid tube allowing to greatly improve surgical procedure operations, with a great reduction of the materials and means necessary to perform such a procedure, while reducing the operation time, blood leakages, vasal traumas, and finally facilitating a closure of the puncturing situ.

According to one aspect of the present invention, the above mentioned aim and objects, as well as yet other objects, which will become more apparent hereinafter, are achieved by a variable diameter tube, to be used as a vasal inserter in hemodynamic research and related operations, characterized in that said tube is made by coupling two materials having different properties, said materials being so connected as to provide a single rigid and stretchable article of manufacture.

BRIEF DESCRIPTION OF THE DRAWINGS

Further characteristics and advantages of the present invention will become more apparent hereinafter from the following detailed disclosure of a preferred, though not exclusive, embodiment of the invention, which is illustrated, by way of an indicative, but not limitative, example in the accompanying drawings, where.

DESCRIPTION OF THE PREFERRED EMBODIMENTS

With reference to the number references of the above mentioned figures, the variable diameter and stretchable tube according to the present invention, which has been generally indicated by the reference number 1, consists of a rigid tube element having a stretchable or adjustable diameter, which is made by coupling two materials having different characteristics, said materials being so coupled as to provide a single rigid and stretchable article of manufacture or tube assembly.

In particular, the required stiffness properties are achieved by using an extruded tubular element made of PEEK, i.e. a thermoplastic polyketone polymeric material.

This material has been already used in the medical field, even for forming implanting devices, and can also be used in a carbon fiber stiffened construction, even if it is per se greatly strong.

The required resilient properties are achieved, on the contrary, by using another polymer, that is linear polyurethane PU.

The latter can be processed by holding, extruding, dipping methods and so on.

In a low hardness formulation, it is very soft and has very good resilient properties.

Another material having very satisfactory resilient and strength properties, of an elastomeric nature, is the silicone material.

Figure 1:
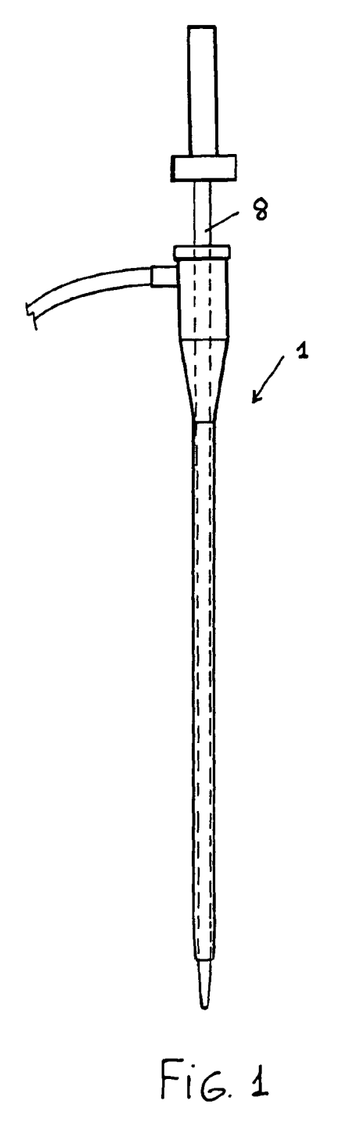
FIG. 1 is an elevation view of the variable diameter tube according to the present invention, with an inserter engaged therein.
Figure 2:
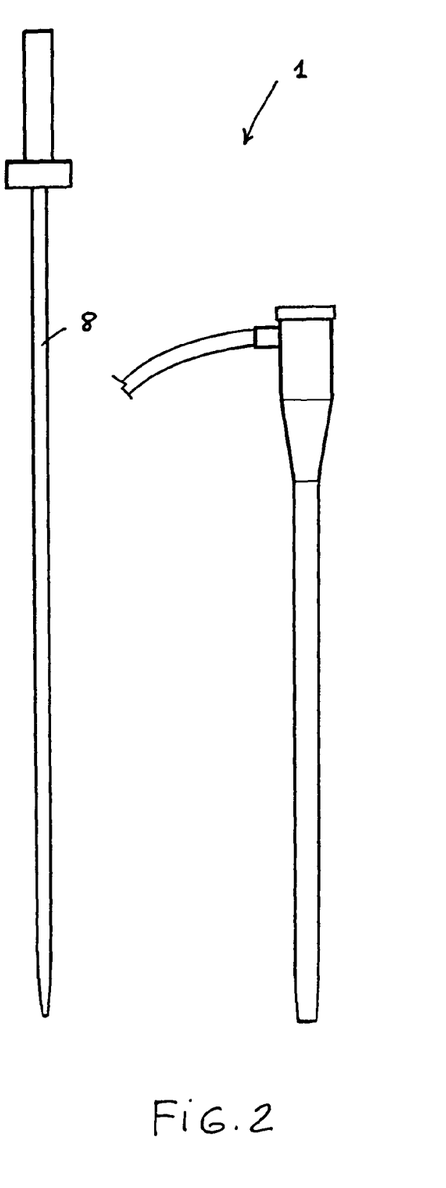
FIG. 2 is an exploded view showing the variable diameter tube to be fitted to a dilator according to the invention.
Figure 3:
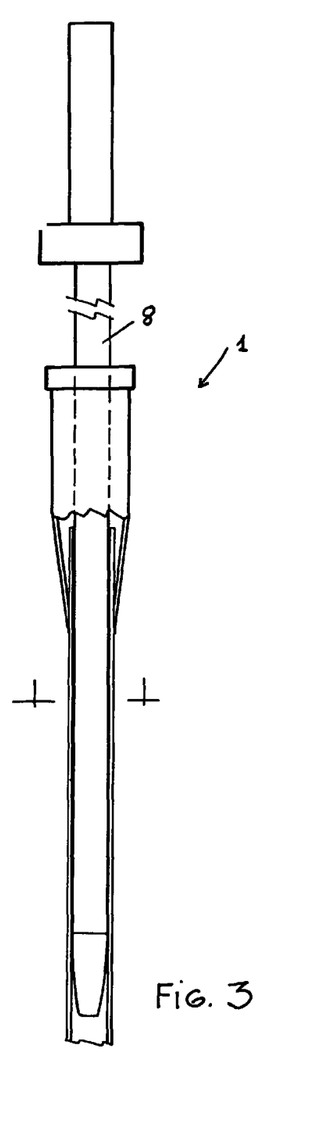
FIG. 3 is a partially cross-sectioned elevation view showing a procedure for inserting a dilatator or dilating device, or other devices of less diameter.
Figure 4:
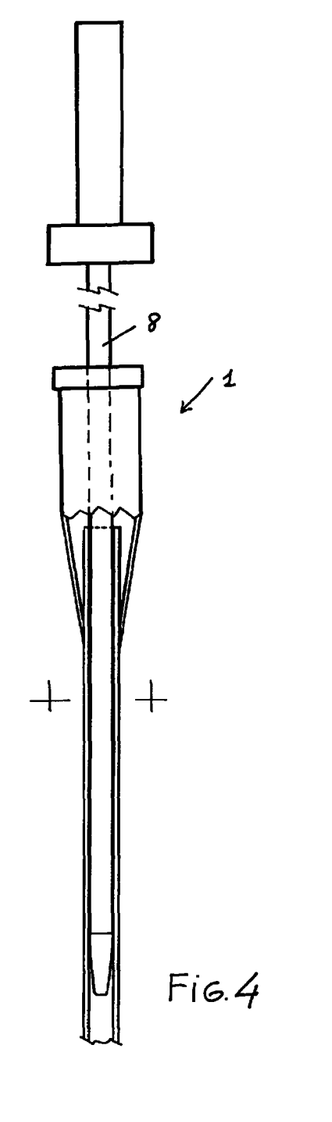
FIG. 4 is a further partially cross-sectioned elevation view, similar to FIG. 3, but showing an insertion of larger diameter dilatator devices.
Figure 5:
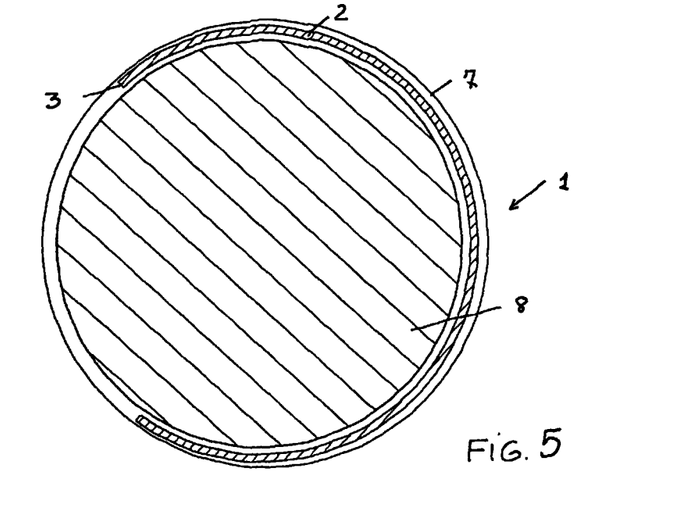
FIG. 5 is a cross-sectional view of a stretchable or variable diameter tube according to the present invention, with a "sandwich" construction, and with an inserter engaged therein.
Figure 7:
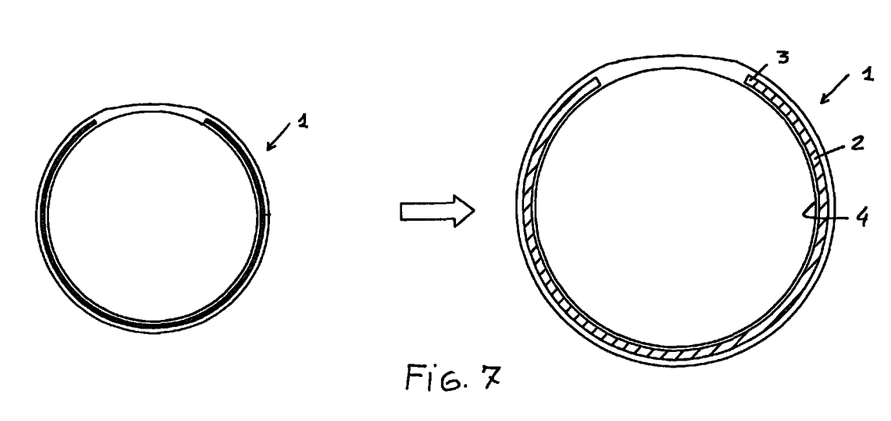
FIG. 7 shows two cross-sectional views, one of which on an enlarged scale, of the variable diameter or stretchable tube according to the present invention, with said sandwich construction.
Figure 8:
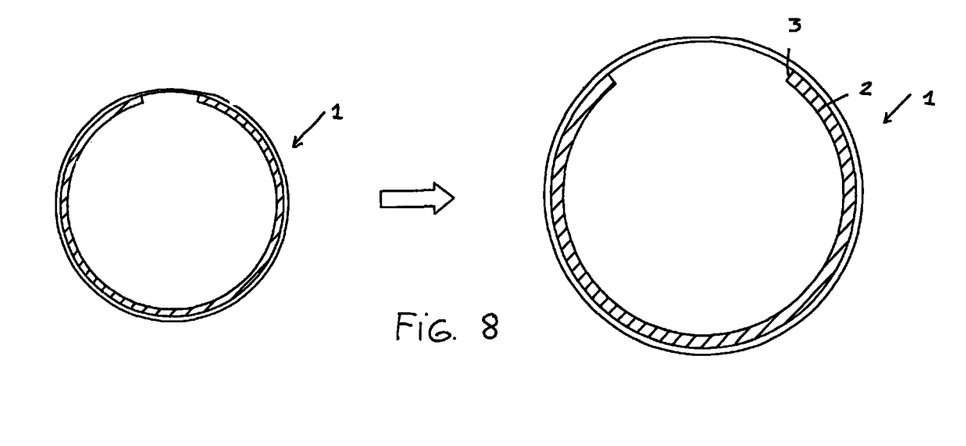
FIG. 8 shows two further cross-sectional views, one of which on an enlarged scale, of the variable diameter tube according to the present invention, having the mentioned bilayer construction.

According to a first embodiment, the variable diameter tube 1 has a "sandwich" construction.

Since the two above mentioned materials are not compatible with one another, in particular PEEK being an inert material which cannot be embedded in the PU material, the variable diameter or stretchable tube according to the present invention is made by a method comprising the following method steps.

The first step provides to extrude the rigid tubular element, generally indicated by the reference number 2, having a target or set inner diameter (for example 3.1 mm and 3.2 mm in outer diameter).

This tubular element 2 is accordingly longitudinally cut, for example along a single directrix line 3.

The thus opened tubular element 2 has a rest diameter of substantially 3.1 mm, and it can be properly stretched.

The second method step provides to make by extruding, or preferably dipping, a tubular element 4 of thin thickness, starting from a resilient material, having an outer diameter of 3.1 mm.

The thus made rigid tubular element 2 is accordingly fitted on the tubular soft element 4.

A first step provides to extrude a rigid PEEK tubular element, 2 having a target or set inner diameter (for example an inner diameter of 3.1 mm and 3.2 mm in outer diameter).

Then, in a further step is the tubular element 2 is longitudinally cut, for example along a single directrix line 3.

The thus formed longitudinally cut tubular element 2 has a rest diameter of substantially 3.1 mm, and it can be properly stretched.

Then, in a further step a second tubular element 4 of this thickness, is made starting from a resilient linear polyurethane material, having an outer diameter of 3.1 mm.

The thus made rigid tubular element 2 is then fitted on the tubular soft element 4.

A third soft tubular element 5 is then machined to an inner diameter equal to the outer diameter of the rigid tubular element 2, that is 3.2 mm.

The rigid tubular element 2, in particular, is then arranged with a sandwich arrangement between the two soft materials which are then sealed or welded to one another, both at the end portions of the tube and along the cut 6 of the rigid tubular element 2.

Thus, is herein achieved a three-layer tube formed by coupling the soft and rigid tubular elements, and which can be stretched along the cut 6 performed along a directrix line of the rigid tubular element.

In this connection it should be pointed out that it is also possible to provide several cuts, suitable arranged with respect to one another. Additionally, in some embodiments, the rigid tubular element may comprise a C-shaped cross-section.

The end tube 1 will have, in a rest condition, the starting diameter of the rigid tube.

The stretching of the tube is not a permanent one.

The slippery properties of the end tube can be improved by using suitable lubricating or coating materials, as those which are conventionally used in the medical field.

Figure 6:
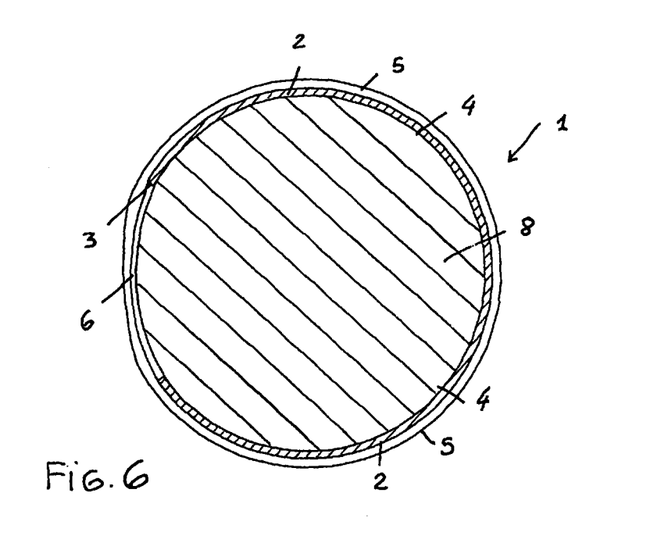
FIG. 6 is a further cross-sectional view of a variable diameter and stretchable tube having a "bilayer" configuration, with an inserter engaged therein.

According to a further embodiment of the invention, the variable diameter or stretchable tube 1 according to the present has a bilayer construction, as schematically shown in FIG. 6.

A removal of the inner soft tube, while leaving the rigid tubular, element 2, made of a PEEK materials, as a first layer, and an outer tubular element 7, made of a PEEK material, as an outer layer, would provide the advantage that it would not be necessary to use outer lubricating materials, since, as known, PEEK has a very low coefficient of friction.

The two above layers are coupled to one another by specifically designed gluing materials or by any other desired technical methods.

Accordingly, the above disclosed variable diameter tube 1 is adapted to resiliently modify its diameter, thereby it can be stretched to a larger diameter.

Figure 9:
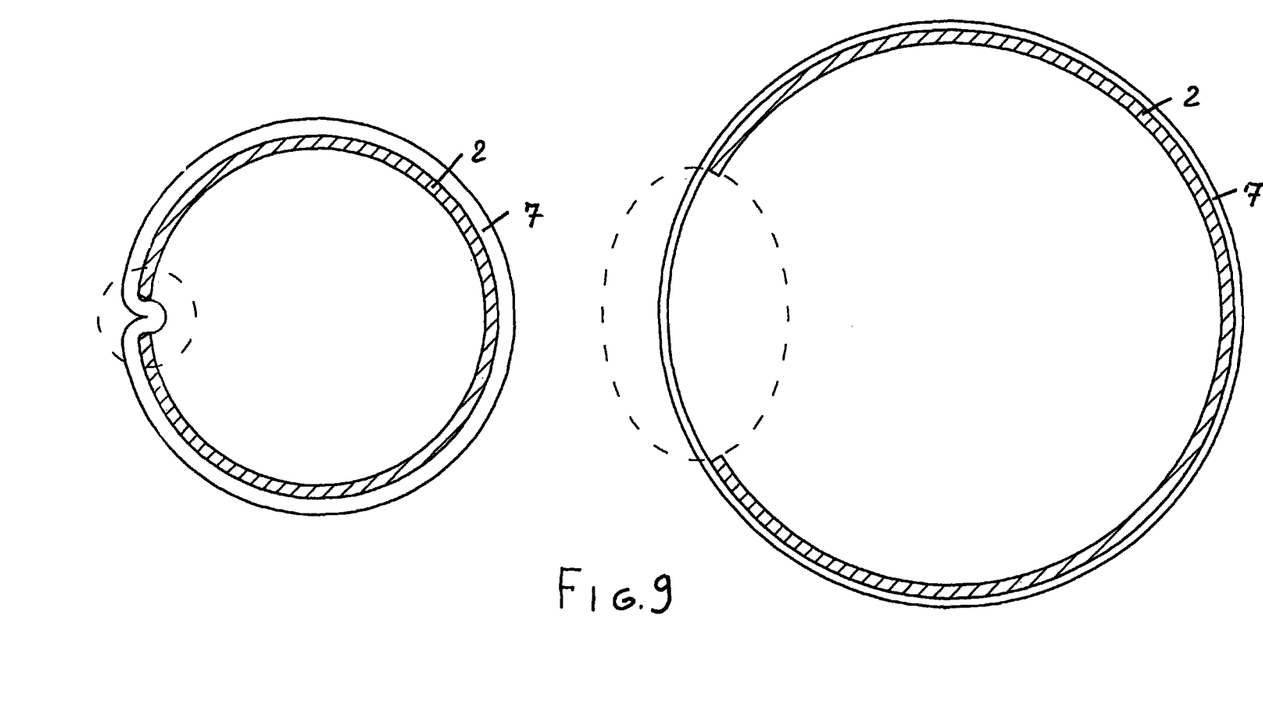
FIG. 9 shows two further cross-sections of the variable diameter tube according to the present invention, including so-called "pence" or lug arrangements.

In this connection it should be pointed out that the soft material elements, shown in the drawings by the reference numbers 4, 5, 7, could have an inner diameter larger than the above discussed minimum diameter.

In such an arrangement, the stiffener element, shown in the drawings by the reference number 2, as joined to the corresponding soft elements, will provide a variable diameter or stretchable tube 1 having a "pence" or lug-flap of soft material, which can be directed either toward the inside or the outside of the tube 1.

The presence of such a material excess would be useful for providing the tube 1 with an improved stretching capability, since the element 4+5 or 7 can be generally expanded to an expanding or stretching degree larger than a standard arrangement or, the expanding or stretching being the same, it will have a less tension and, accordingly, a less breaking risk.

In particular, the tube 1 can comprise a portion including the above mentioned "pence" or excess material part, for example near the valve, and a standard part, for example up to the tip of the inserter.

The tube diameter, in particular, is modified by the material being inserted or engaged in the inserter device: for example, as a catheter 8 having a diameter of 4 mm is herein inserted, the stretchable tube will modify its diameter from 3 mm to 4 mm.

The enlarger diameter position, in particular, will correspond to a yielding limit of the soft tube.

The receptive capability limit of the inserter will depend on the valve arranged at the inlet of said inserter, the resilient or elastic properties of its material and the layer geometrical arrangement.

The middle positions will vary from a round configuration to an oval configuration, which is hindered by the material engaged in the inserter.

The rest position will be that of less diameter, defined by the multilayer tube geometry.

The tip of the tube is a tapering tip, and accordingly it will be atraumatic.

In particular, as the subject variable diameter tube is engaged in a vessel, and without any catheters therein, it will be recovered to the above diameter.

In some conditions, it would be desirable to provide an inserter device designed for having a diameter larger than that its rest diameter.

In such a case, it is provided to use a second rigid tube adapted to hold in a pervious and rigid condition the stretchable tube.

To that end it is possible to use a PEEK tube, of a thin thickness, extruded to a desired diameter, to be arranged within the stretchable tube. Said tube, in particular, will be engaged in the inserter through the dilator and then it will be left in said inserter.

It has been found that the invention fully achieves the intended aim and objects.

In fact, the invention provides a rigid tube that is having rigid properties with respect to the inserter body, which is adapted to adjust its diameter, starting from a minimum value to the diameter of the device to be inserted.

Moreover, and this represents the main feature of the present invention, the subject tube is adapted to recover its starting diameter.

Thus, the use of the variable diameter inserter will greatly improve the surgical procedure in which an inserter is used, while providing the following advantages:

a great reduction of the material required for performing the procedure;
a great reduction of the operational times;
a great reduction of bleeding due to replacement operations;
a great reduction of risks associated with a relocating of an inserter;
a great reduction of the vessel traumas due to several puncturing operations;
a great improving of the puncture place closure;
an easy adjusting of the inserter to a lot of dimensions of the device to be inserted.

In practicing the invention, the used materials, as well as the contingent size and shapes, can be any, depending on requirements.

The invention claimed is:

1. A variable diameter tube, comprising:
a first material layer comprising a C-shaped cross-section, the first material layer comprising polyether ether ketone and only one longitudinal cut; and
a second material layer comprising polyurethane, wherein the second material layer is coupled to the first material layer along an outside surface of the first material layer such that the second material layer is disposed around the first material layer, wherein the second material layer is not coupled to lateral surfaces of the longitudinal cut, the variable diameter tube configured to transition between a rest condition, wherein the variable diameter tube has a rest diameter, and an enlarged diameter condition, wherein the variable diameter tube has an enlarged diameter;
wherein the second material layer is flexible such that a displacement between the lateral surfaces of the longitudinal cut increases as an object having a diameter that is greater than the rest diameter of the variable diameter tube is inserted into the variable diameter tube,
wherein the second material layer is more resilient than the first material layer such that transition of the variable diameter tube from the rest condition to the enlarged diameter condition increases the displacement between the lateral surfaces of the longitudinal cut and stretches at least a portion of the second material layer; and
wherein the second material layer defines a folded flap, the folded flap extending inward between the lateral sides of the longitudinal cut when the variable diameter tube is in the rest condition.

2. The variable diameter tube of claim 1, wherein the first material layer further comprises carbon fiber reinforcing components.

3. The variable diameter tube of claim 1, wherein the second material layer has a shape memory in that it returns to the rest diameter when unconstrained.

4. The variable diameter tube of claim 3, wherein the rest diameter is about 3.2 mm.

5. The variable diameter tube of claim 1, further comprising a lubricating material disposed on the first material layer.

6. The variable diameter tube of claim 1, wherein the first material layer is glued to the second material layer.

7. The variable diameter tube of claim 1, wherein the diameter of the variable diameter tube is variable by at least one millimeter between the rest condition and the enlarged diameter condition.

8. A variable diameter tube, comprising:
a first material layer comprising a C-shaped cross-section, the first material layer comprising polyether ether ketone and only one longitudinal cut; and
a second material layer comprising polyurethane, wherein the second material layer is coupled to the first material layer along an outside surface of the first material layer, wherein the second material layer is not coupled to lateral surfaces of the longitudinal cut, the variable diameter tube configured to transition between a rest condition and an enlarged diameter condition;
wherein the second material is flexible such that a displacement between the lateral surfaces of the longitudinal cut increases as an object having a diameter that is greater than a rest diameter of the variable diameter tube is inserted into the variable diameter tube,
wherein the second material is more resilient than the first material such that when the variable diameter tube transitions from the rest condition to the enlarged diameter condition the displacement between lateral surfaces of the longitudinal cut increases and at least a portion of the second material stretches;
wherein the second material is disposed around the first material; and
wherein the second material defines a U-shaped folded flap that extends radially inward between the lateral surfaces of the longitudinal cut when the variable diameter tube is in the rest condition such that the displacement between the lateral surfaces of the longitudinal cut is completely occupied by a portion of the U-shaped folded flap of the second material layer.

9. The variable diameter tube of claim 8, wherein the diameter of the variable diameter tube is variable by at least one millimeter between the rest condition and the enlarged diameter condition.

10. The variable diameter tube of claim 1, wherein the folded flap is U-shaped.

* * * * *